(12) United States Patent
van der Westhuizen (10) Patent No.: US 10,101,221 B2
(45) Date of Patent: Oct. 16, 2018

(54) APPARATUS FOR TESTING THE DEGREE TO WHICH MEAT IS COOKED

(71) Applicant: Valorous Enterprise Ltd, New Malden (GB)

(72) Inventor: Andries Marthinus van der Westhuizen, New Malden (GB)

(73) Assignee: Valorous Enterprise Ltd, Surrey (GB)

( * ) Notice: Subject to any disclaimer, the term of this patent is extended or adjusted under 35 U.S.C. 154(b) by 0 days.

(21) Appl. No.: 15/520,295

(22) PCT Filed: Oct. 26, 2015

(86) PCT No.: PCT/GB2015/000294
§ 371 (c)(1),
(2) Date: Apr. 19, 2017

(87) PCT Pub. No.: WO2016/066984
PCT Pub. Date: May 6, 2016

(65) Prior Publication Data
US 2018/0010970 A1    Jan. 11, 2018

(30) Foreign Application Priority Data
Oct. 29, 2014 (GB) .................................. 1419291.8

(51) Int. Cl.
*G01L 1/00* (2006.01)
*G01L 1/16* (2006.01)
*G01N 33/12* (2006.01)

(52) U.S. Cl.
CPC ................ *G01L 1/16* (2013.01); *G01N 33/12* (2013.01)

(58) Field of Classification Search
CPC .................................. G01L 1/16; G01N 33/12
USPC ....................................................... 73/862.68
See application file for complete search history.

(56) References Cited

U.S. PATENT DOCUMENTS

| 3,078,710 A | 2/1963 | Palmer |
| 3,732,727 A | 5/1973 | Hinnergardt et al. |
| 3,956,924 A * | 5/1976 | Hansen ..................... G01N 3/42 73/81 |
| 4,052,890 A | 10/1977 | Kammlah et al. |

(Continued)

FOREIGN PATENT DOCUMENTS

| EP | 0916947 A1 | 5/1999 |
| GB | 2167568 A | 5/1986 |

(Continued)

*Primary Examiner* — Max Noori
(74) *Attorney, Agent, or Firm* — Iandiorio Teska & Coleman, LLP (57) ABSTRACT

Apparatus (2) for testing the degree to which meat (3) is cooked, which apparatus (2) comprises: (i) a body (4); (ii) a meat-engaging formation (6) which is fixed with respect to the body (4); (iii) a probe (8) which is movable with respect to the body (4), and which is configured such that in use it does not penetrate the meat (3); (iv) sensor means (10) for sensing the force applied by the meat (3) to the probe (8) when the meat-engaging formation (6) is placed on the meat (3); (v) processor means (12) which operates consequent upon the force sensed by the sensor means (10) to provide an indication of the degree to which the meat is cooked; and (vi) test result means (14) for giving the indication provided by the processor means (12) as a visual and/or audible test result.

15 Claims, 8 Drawing Sheets

(56) References Cited

U.S. PATENT DOCUMENTS

| | | | | |
|---|---|---|---|---|
| 4,856,318 A | * | 8/1989 | Hogan | G01N 3/303 |
| | | | | 73/12.13 |
| 4,939,574 A | * | 7/1990 | Petersen | A22B 5/007 |
| | | | | 348/89 |
| 5,099,682 A | | 3/1992 | Denomme et al. | |

FOREIGN PATENT DOCUMENTS

| | | |
|---|---|---|
| GB | 2438641 A | 12/2007 |
| WO | WO 91/19976 A1 | 12/1991 |
| WO | 03079005 A2 | 9/2003 |

* cited by examiner

APPARATUS FOR TESTING THE DEGREE TO WHICH MEAT IS COOKED

This invention relates to apparatus for testing the degree to which meat is cooked.

Hitherto, the degree to which meat is cooked has predominantly been tested by various types of thermometer apparatus, or manually by a person using their fingers. The thermometer apparatus is not satisfactory in a number of respects. More especially, the thermometer apparatus is time consuming to use. Also the use of the thermometer apparatus requires exact and detailed actions, and these can be awkward during a cooking process, especially when a person is cooking under pressure, for example in a commercial kitchen. Specialised knowledge of how to use the thermometer apparatus is required, along with a specialised knowledge of temperature ranges. The thermometer apparatus requires that the meat be punctured multiple times during the course of the cooking and this may lead to hygiene and preparation quality problems. The manual testing of the meat by a person using their fingers is also not satisfactory in a number of respects. More specifically, the manual testing of the meat by a person using their fingers requires experience and specialised knowledge. Results can be inconsistent since they depend upon the judgement of the person testing the firmness of the meat with their fingers, and this judgement may vary from person to person. Also, touching the meat with fingers can be unhygienic.

It is an aim of the present invention to obviate or reduce the above mentioned problems.

Accordingly, the present invention provides apparatus for testing the degree to which meat is cooked, which apparatus comprises:

(i) a body;
(ii) a meat-engaging formation which is fixed with respect to the body;
(iii) a probe which is movable with respect to the body, and which is configured such that in use it does not penetrate the meat;
(iv) sensor means for sensing the force applied by the meat to the probe when the meat-engaging formation is placed on the meat;
(v) processor means which operates consequent upon the force sensed by the sensor means to provide an indication of the degree to which the meat is cooked;
(vi) test result means for giving the indication provided by the processor means as a visual and/or audio test result; and
(vii) selector means for selecting the approximate thickness of the meat.

The apparatus of the present invention is advantageous in that it is able to provide test results much faster than the known thermometer apparatus. The apparatus of the present invention can do multiple tests of different items of meat in quick succession. The apparatus of the present invention is simple to use and does not require extensive knowledge or experience. The apparatus of the present invention does not require penetration of the meat. The apparatus of the present invention is able to provide more accurate and consistent results than a person manually using their fingers. The apparatus of the present invention is also able to be more hygienic in use than a person using their fingers.

The meat being tested may be steak, for example beef steak. Other types of meat may be tested including, for example, beef, lamb, pork and poultry. The apparatus of the present invention may be manufactured and sold for testing one type of meat only. Alternatively, the apparatus of the present invention may be manufactured and sold for testing more than one type of meat. Where the apparatus is for testing more than one type of meat, then the processor means may be such that it is able to provide an indication of the degree to which each different type of meat is cooked. The appropriate information for the type of meat being tested may be achieved by means of a selector switch, for example a rotatable selector switch rotatable to a variety of different positions for different types of meat.

The apparatus may be one in which the apparatus includes biasing means which biases the probe to a ready-for-use position in which the probe extends beyond the meat-engaging formation. If desired, the probe may be one which does not move. In this case, the sensor means may be effective simply to transfer the applied pressure from the probe to the processor means.

When the probe is a movable probe, then the apparatus may be one in which the probe is movable by sliding backwards and forwards in the body. Other types of movable probe may be employed, for example a pivoting probe.

The biasing means is preferably a spring biasing means. Other types of biasing means may be employed. The spring biasing means is preferably a coil spring. Preferably the coil spring is a conical coil spring. The coils of the conical spring are able to compress within each other so that the conical spring is able to compress to a smaller size than a standard coil spring. Also, the coils of a conical coil spring are able to compress without resting on adjacent coils of the spring.

Where the spring biasing means is a coil spring, then the coil spring may compress within a range of 0-10 mm. The coil spring may such that it is able to transfer up to 1 Kg force (9.81N). Other types of spring biasing means may be employed so that, for example, the spring biasing means may be a leaf spring.

The apparatus may be one in which the biasing means acts on an end of the probe remote from an end of the probe that extends beyond the meat-engaging formation. In this case, the apparatus may be one in which the end of the probe that extends beyond the meat-engaging formation is compressible to be level with an outer surface of the meat-engaging formation before the biasing means fully compresses, thereby to limit the force able to be exerted on the sensor. The limiting of the force able to be exerted on the sensor may be such as to ensure that the sensor is not exposed to a force which is beyond safe or recommended loading limits. Further, the apparatus may be one in which the end of the probe that extends beyond the meat-engaging formation is a domed head, and in which the end of the probe remote from the domed head is the end of a shank portion of the probe.

The domed head preferably has a diameter of from 8.5-14.3 mm. A dome of such a diameter may have a height of from 4-11 mm. A preferred dome formation is one having a diameter of 14.3 mm and a height of 11 mm. Examples of other domes are one having a diameter of 11.7 mm and a height of 6 mm, and another dome having a diameter of 8.5 mm and a height of 4.mm. The domed head may be of other dimensions if desired.

When the probe is a movable probe, then the apparatus may be one in which the probe includes stop means for stopping the probe in the ready-for-use position. The stop means may be a shoulder formed on the shank portion of the probe, the shoulder being such that it abuts against a shoulder in the housing.

The body is preferably constructed for being held in a user's hand. However, if desired, the body may form part of a non-hand held device, for example a free standing device, for example a free standing device for standing on a kitchen work surface.

The body may be a tubular body. The body may be of other shapes if desired.

The apparatus may be one in which the meat-engaging formation is at one end of the body. The meat-engaging formation may be positioned at other parts of the body if desired, for example a middle part of the body.

The meat-engaging formation may be configured such that it does not penetrate the meat. It may however penetrate the meat if desired. The meat-engaging formation may be a planar formation. The meat-engaging portion may alternatively be a curved formation or a rounded formation. The meat-engaging formation may include a flange which extends outwardly from the body. The flange may increase the surface area of the meat-engaging formation, for example in order to provide increased stability of the apparatus on the meat.

The sensor means may be a transducer sensor means such for example as a piezoelectric transducer sensor means. Other transducer sensor means for transforming pressure into electric signals may be employed so that, for example the transducer sensor means may be a strain gauge.

The sensor means may be one in which is able to provide accurate and repeatable values over a range of forces from 0-1 Kg (0-9.81N). Other force ranges may be employed.

The processor means may be any suitable and appropriate type of processor means. Typically the processor means is a microprocessor means, for example an 8 bit microcontroller. The 8 bit microcontroller may be, for example a PIC16f88 microcontroller as manufactured by Microchip. The processor means will normally contain a program which enables the processor means to provide the indication of the degree to which the meat is cooked. The indication of the degree to which the meat is cooked is then able to be provided on the display means.

The apparatus may include battery-receiving means for receiving at least one battery, whereby the apparatus is battery operated. Alternatively or additionally, the apparatus may be mains operated.

The test result means may give just a visual test result. Alternatively or additionally, the test result means may give an audio test result. The visual test result means may be given using lights or a screen. The audio test result may be in the form of a beep or recorded words. The visual test result and/or the recorded test result may be such as to provide one or more of the values of blue, rare, medium rare, medium, medium well done, and well done. Other values may be provided.

The apparatus may include time delay means whereby the processor means captures the mean resistance reading from the sensor means after a predetermined time period which commences with the meat-engaging formation being placed on the meat, whereby the meat surface is allowed to settle prior to a result being obtained. The use of the time delay means may increase the accuracy of the operation of the apparatus of the present invention. The time delay means may be any suitable and appropriate electrical or electronic time delay means. The time delay means may also be a mechanical time delay means. The time delay means may be included in a program in the processor means.

The selector means may operate to control the processor means such that the values in the processor means for giving the indication of the degree to which the meat is cooked are re-set in dependence upon the selected meat thickness.

The apparatus may include moisture-preventing means for preventing the entrance of moisture into the body via the probe.

The moisture-preventing means may be a cover which extends over the probe. Other moisture-preventing means may be employed so that, for example, the moisture-preventing means may alternatively be one or more seals positioned between the probe and the body of the apparatus. Where the moisture-preventing means is a cover, then the cover may be a resiliently-deformable cover. The cover may be a removable cover. The removable cover may be secured in position by being a clip fit, a press fit, a screw fit, or a bayonet-type twist fit. Other securing means may be employed.

Embodiments of the invention will now be described solely by way of example and with reference to the accompanying drawings in which.

Referring to FIGS. 1-5, there is shown apparatus 2 for testing the degree to which meat 3 is cooked. The apparatus 2 comprises a body 4 which is constructed for being held in a users hand. The apparatus 2 also comprises a meat-engaging formation 6. The meat-engaging formation 6 is fixed with respect to the body 4. The meat-engaging formation 4 is configured such that in use it does not penetrate the meat 3.

The apparatus 2 further comprises a probe 8. The probe 8 is movable with respect to the body 4. The probe 8 is configured such that in use it does not penetrate the meat 3.

Sensor means 10 is provided for sensing the force applied by the meat to the probe 8 when the meat-engaging formation 6 is placed on the meat. Processor means in the form of microprocessor means 12 operates consequent upon the force sensed by the sensor means 10 to provide an indication of the degree to which the meat 3 is cooked. Test result means 14 gives the indication provided by the microprocessor means 12 as a visual result.

Figure 1:
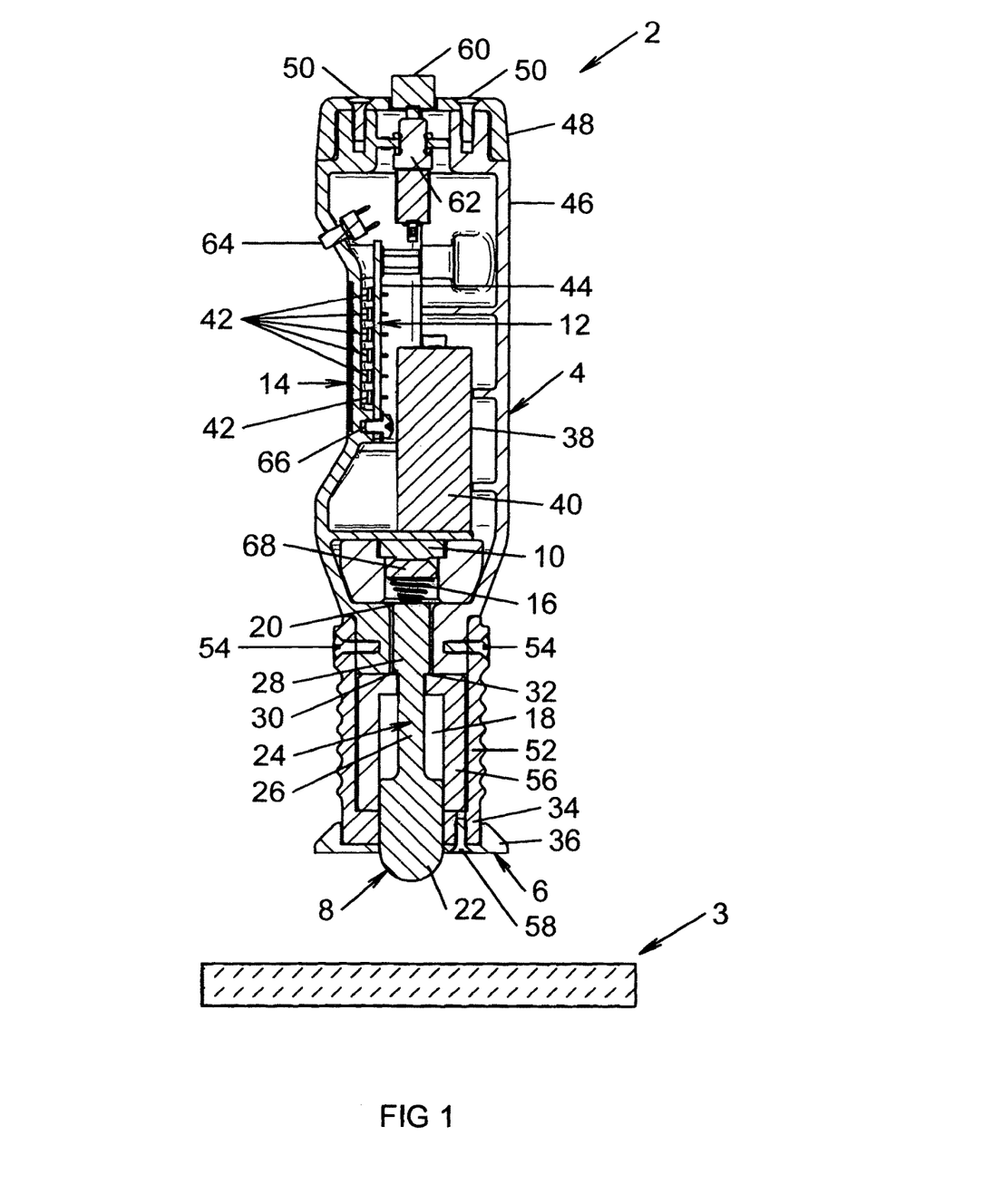
FIG. 1 is a longitudinal section through first apparatus for testing the degree to which meat is cooked.
Figure 2:
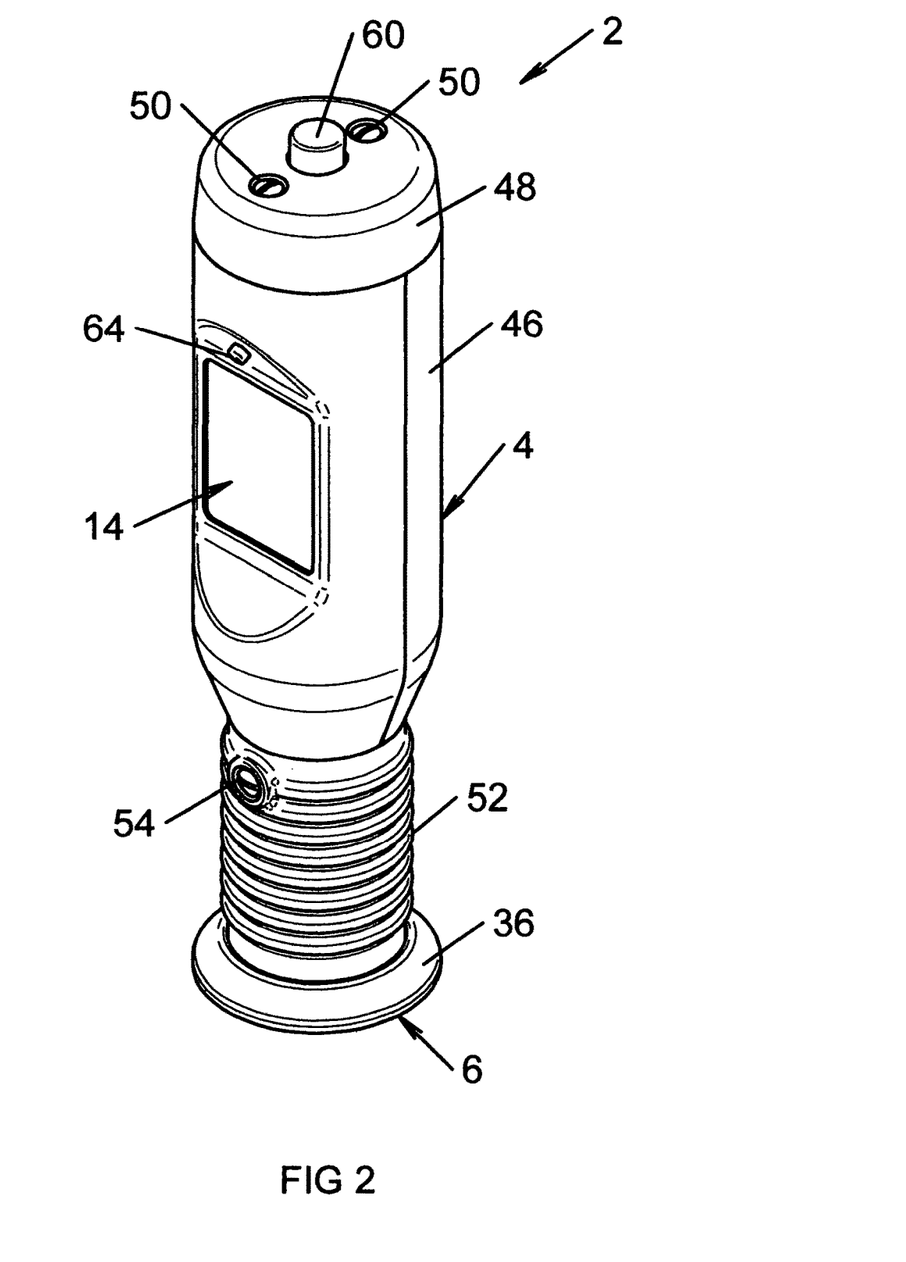
FIG. 2 is a perspective view from the front and one side of the apparatus shown in FIG. 1.
Figure 3:
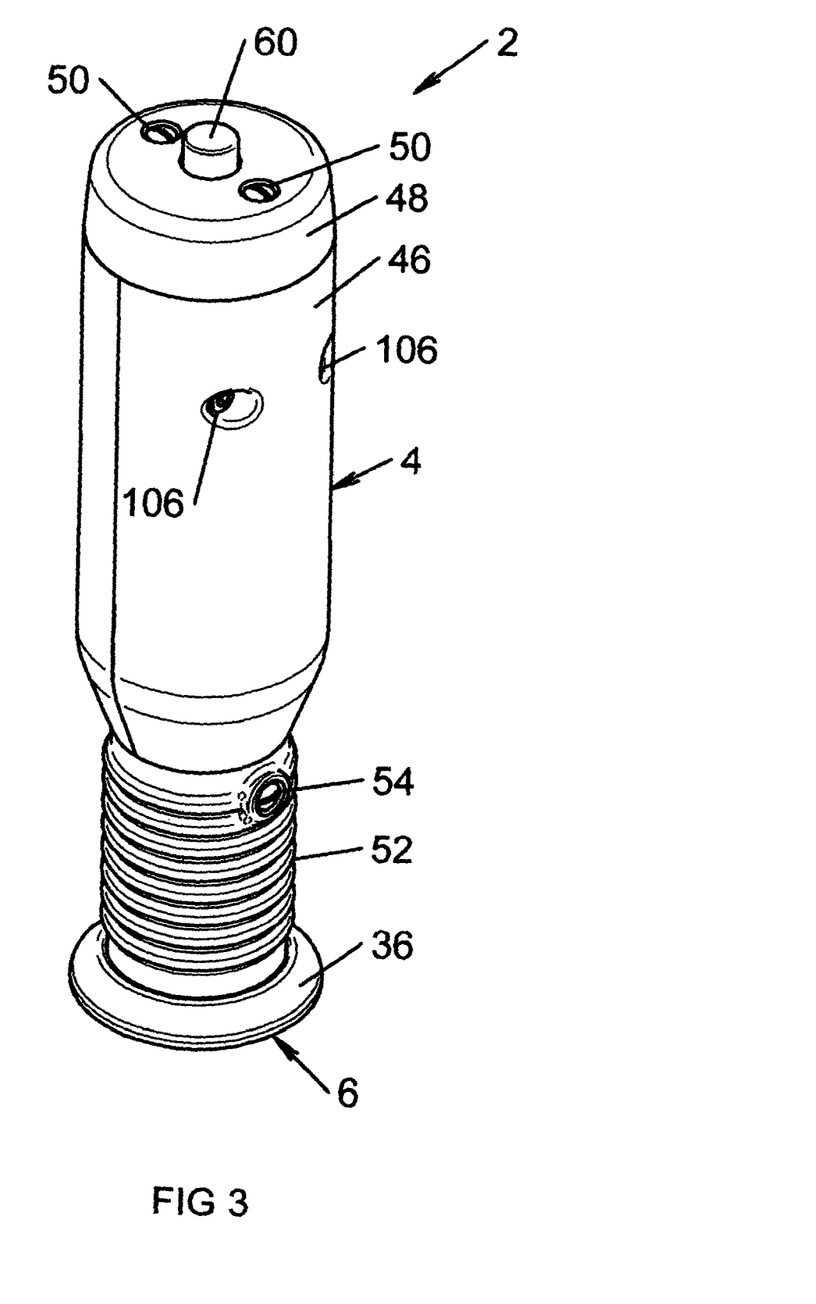
FIG. 3 is a perspective view from the rear and one side of the apparatus shown in FIG. 1.
Figure 4:
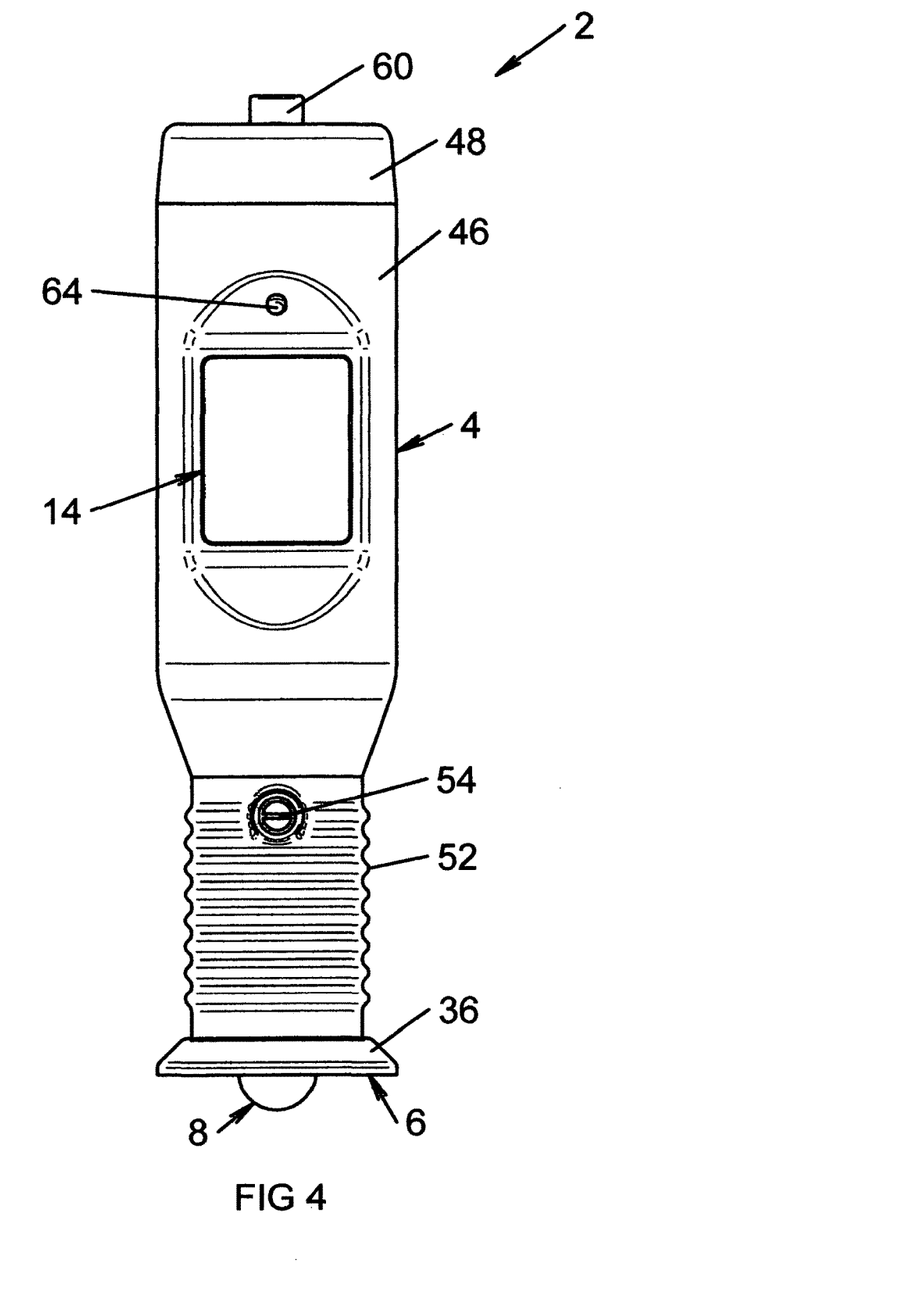
FIG. 4 is a front view of the apparatus shown in FIG. 1.
Figure 5:
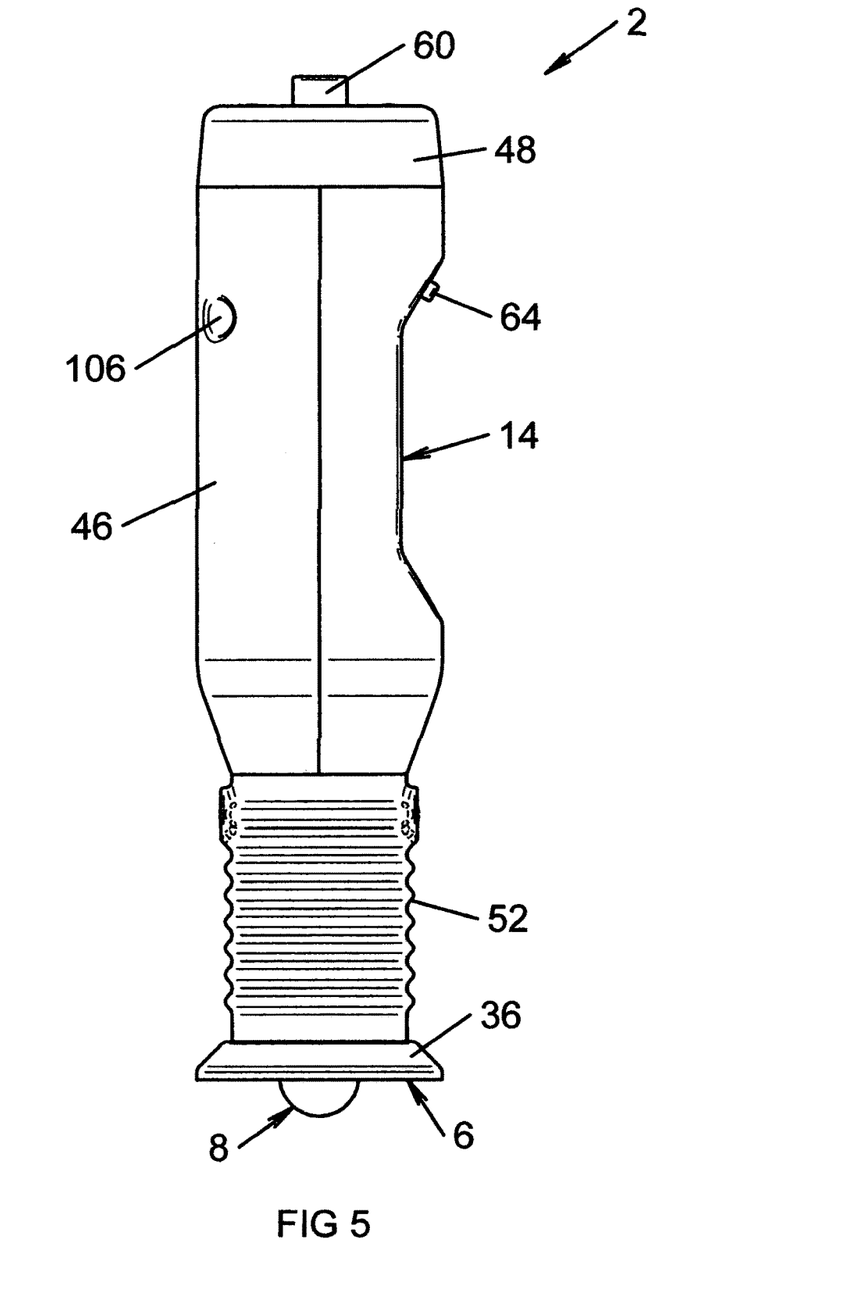
FIG. 5 is a side view of the apparatus shown in FIG. 1.

The apparatus 2 includes biasing means 16 which biases the probe 8 to a ready-for-use position which is shown in FIG. 1, and in which the probe 8 extends beyond the meat-engaging formation 6. The probe 8 is movable by sliding backwards and forwards in a chamber 18 in the body 4. The biasing means 16 is a spring biasing means in the form of a coil spring.

The biasing means 16 acts on an end 20 of the probe remote from the end 22 of the probe 8 that extends beyond the meat-engaging formation 6. The end 22 of the probe 8 that extends beyond the meat-engaging formation 6 is a domed head as shown. The end 20 of the probe 8 remote from the domed head is the end of a shank portion 24 of the probe 8. The shank portion 24 comprises a first portion 26 and a second portion 28. The second portion 28 is of a larger diameter than the first portion 26. A shoulder 30 is formed between the first and second portions 26, 28. This shoulder 30 acts as stop means for stopping the probe 8 in the ready-for-use position. The shoulder 30 abuts against a shoulder 32 in the housing 4.

The meat-engaging formation 6 is at one end 34 of the body 4. The body 4 is a tubular body 4. The meat-engaging formation 6 is a planar formation. The planar formation includes a flange 36 which extends outwardly from the body 4. The flange 36 increases the area of the meat-engaging formation 6. This provides increased stability of the apparatus 2 on the meat 3, and ensures that the meat-engaging formation 6 is able to engage an appreciable area of the meat 3 for obtaining a reading from the meat 3 which is over a meaningful representative area of the meat 3.

The sensor means 10 is a piezoelectric sensor means 10. The microprocessor means is an Intel-microprocessor means 12.

The apparatus 2 includes battery-receiving means in the form of a compartment 38 which receives a battery 40. The battery 40 connects to appropriate terminals so that the apparatus 2 is battery operated.

Figure 9:
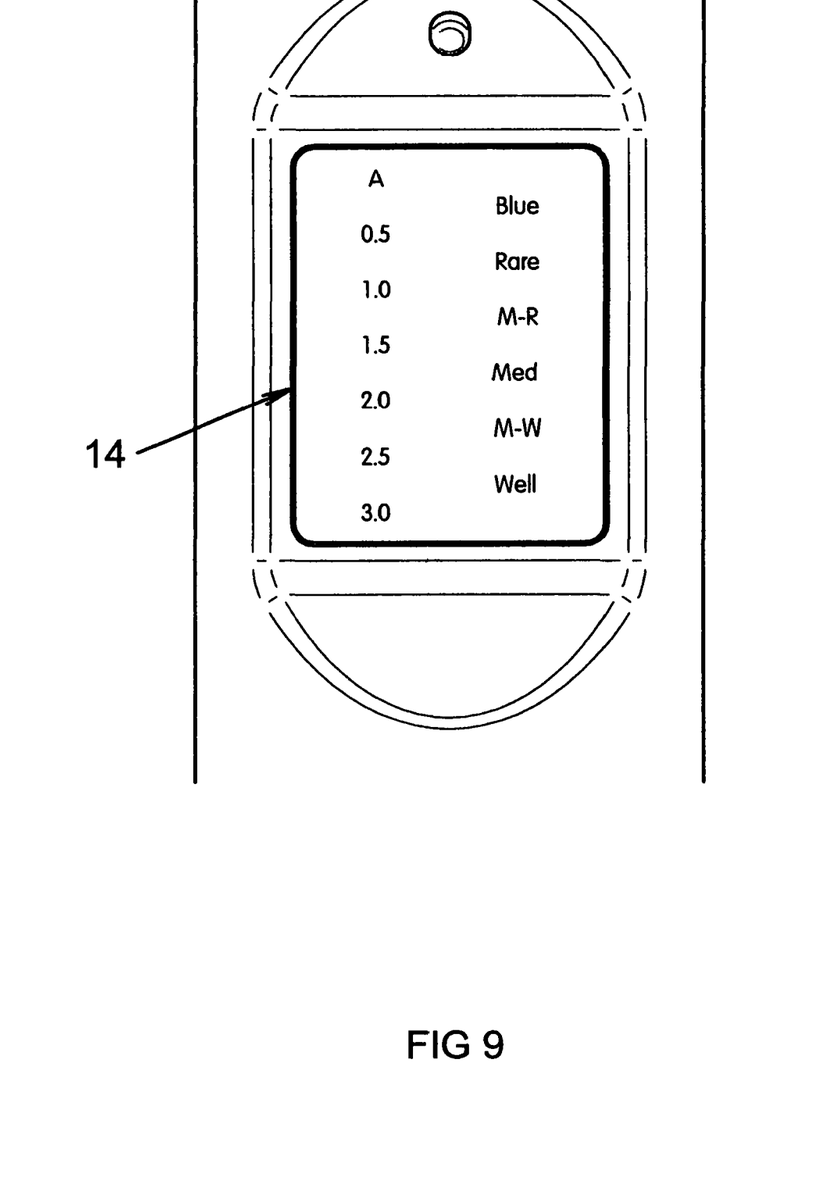
FIG. 9 shows an example display for the display means of the apparatus of the invention.

The test result means 14 is a visual display means. The test result means 14 includes a plurality of light emitting diodes 42. As shown in FIG. 9, the visual display means 14 includes a display with the values blue, rare, medium rare, medium well done, and well done. The display also displays the values of "A", 0.5, 1.0, 1.5, 2.0, 2.5 and 3.0. These values are steak thicknesses in inches. Other values may be employed for other types of meat 3. The letter "A" indicates that the apparatus 2 is operating in an automatic operating mode which uses an average thickness setting as opposed to when the apparatus 2 is set to a specific thickness.

As best seen from FIG. 1, the microprocessor means 12 includes a printed circuit board 44. The body 4 has a main portion 46 and an end portion 48. The end portion 48 secures to the main portion 46 by screws 50. An end portion 52 is corrugated as shown. The end portion 52 secures to the main portion 46 by screws 54. The end portion 52 locates an insert 56 which has the chamber 18 and the shoulder 32. The insert 56 is held in position by the end 34. The meat-engaging formation 6 is secured to the end 34 by one or more screws 58.

The end portion 48 is provided with two buttons, namely an on/off button 60 and a thickness selection button 64. When the on/off button 60 is depressed, it causes movement of an inside portion 62 to enable the apparatus 2 to operate in a selected mode.

The printed circuit board 44 is held in position on the main portion 46 of the body 4 by one or more screws 66. The biasing means 16 is spaced apart from the sensor means 10 by a spacer 68.

In a first alternative embodiment of the apparatus 2, the thickness selection button 64 is altered to a jack 64 to which a data cable can be attached. The data cable may then be attached to a computer for purposes of calibrating the apparatus 2. In a second alternative embodiment of the apparatus 2, the jack 64 may be a power jack for providing a rechargeable facility for the battery. When the jack 64 is a power jack, then the jack 64 will be connected to the battery in order to allow the re-charging.

The apparatus 2 is able to operate in a quick and simple manner in order to obtain multiple tests of the degree to which the meat 3 is cooked. As the degree to which the meat 3 is cooked increases, the degree of firmness of the meat 3 increases. It is this degree of firmness which is sensed by the probe 8 and transmitted via the sensor means 10 to the microprocessor means 12 for display on the display means 14. The apparatus 2 is able to be operated by users with little or no experience or knowledge of the operation of the apparatus 2. The apparatus 2 is able to give consistent and accurate results, and without penetration of the meat 3.

Figures 6, 7, 8:
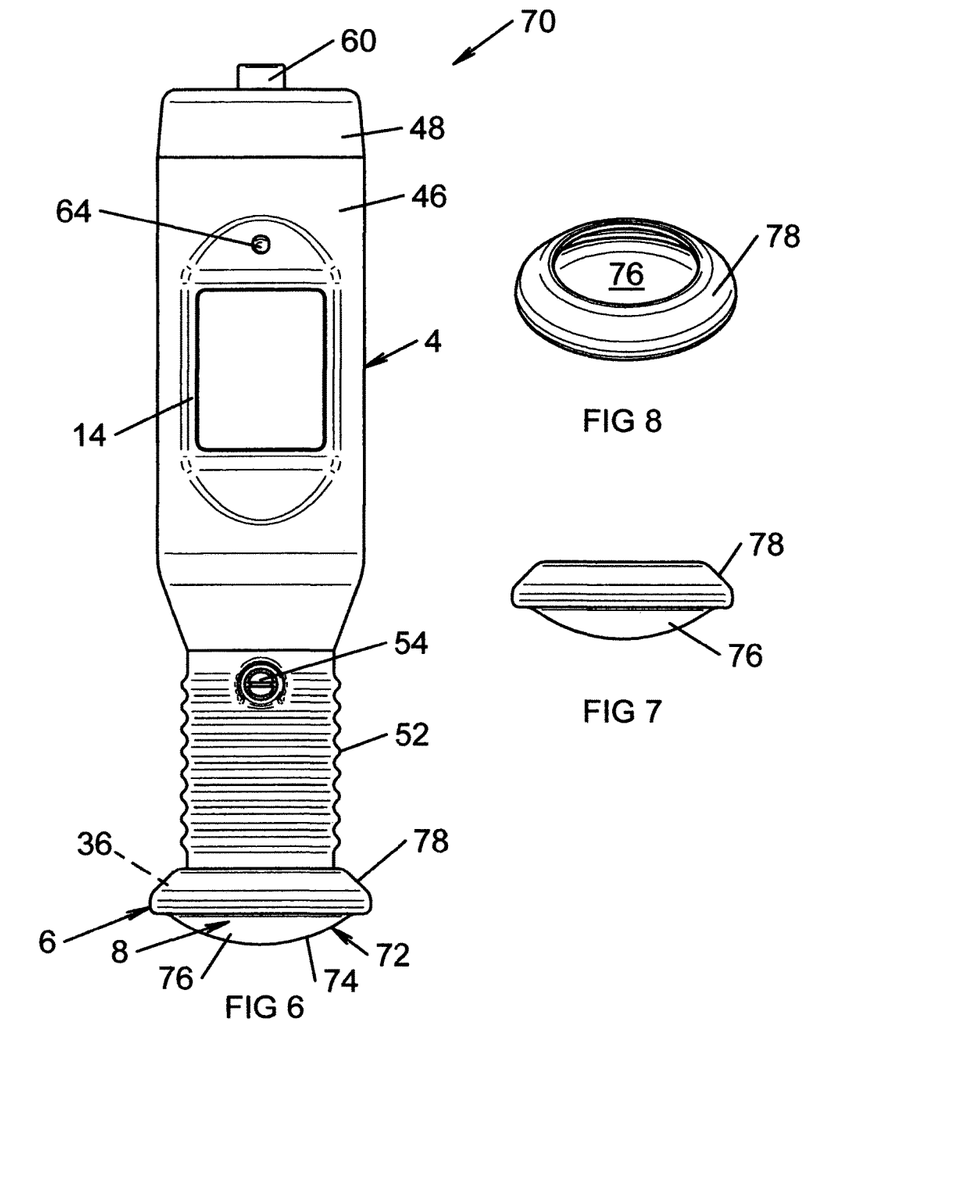
FIG. 6 is a front view like FIG. 4 but of second apparatus for testing the degree to which meat is cooked.
FIG. 7 is a front view of part of the apparatus shown in FIG. 6.
FIG. 8 is a top perspective view of the part of the apparatus shown in FIG. 7.

Referring now to FIGS. 6-8, there is shown second apparatus 70 of the present invention. The apparatus 70 is like the apparatus 2. Similar parts have been given the same reference numerals for ease of comparison and understanding. The apparatus 70 is provided with moisture-preventing means 72 for preventing the entrance of moisture into the body 4 via the probe 8. The moisture-preventing means 72 comprises a resiliently-deformable cover 74 which extends over the probe 8. The cover 74 comprises a dome portion 76 and a ring portion 78. The ring portion 78 can be secured over the meat-engaging formation 6, for example as a press fit, a screw fit or any other suitable and appropriate fit. The dome portion 76 is flexible so that it flexes on contact with the meat 3 to allow the probe 8 to be contacted indirectly by the meat 3. The cover 74 prevents the moisture from the meat 3 entering into apparatus 2 via the probe 8. Because the dome portion 76 is flexible, it allows the pressure from the meat 3 to be transferred to the sensor means 10 which acts as a pressure sensor means. The resilience of the cover 74 is very small compared to the resilience of the meat surface so that the effect of the cover 74 on the accuracy of the apparatus 2 is negligible. Because the cover 74 is flexible, it is able to regain its dome shape when the apparatus 70 is removed from the meat 3. The moisture-preventing means 72 can itself be removable if desired for cleaning.

Figure 10:
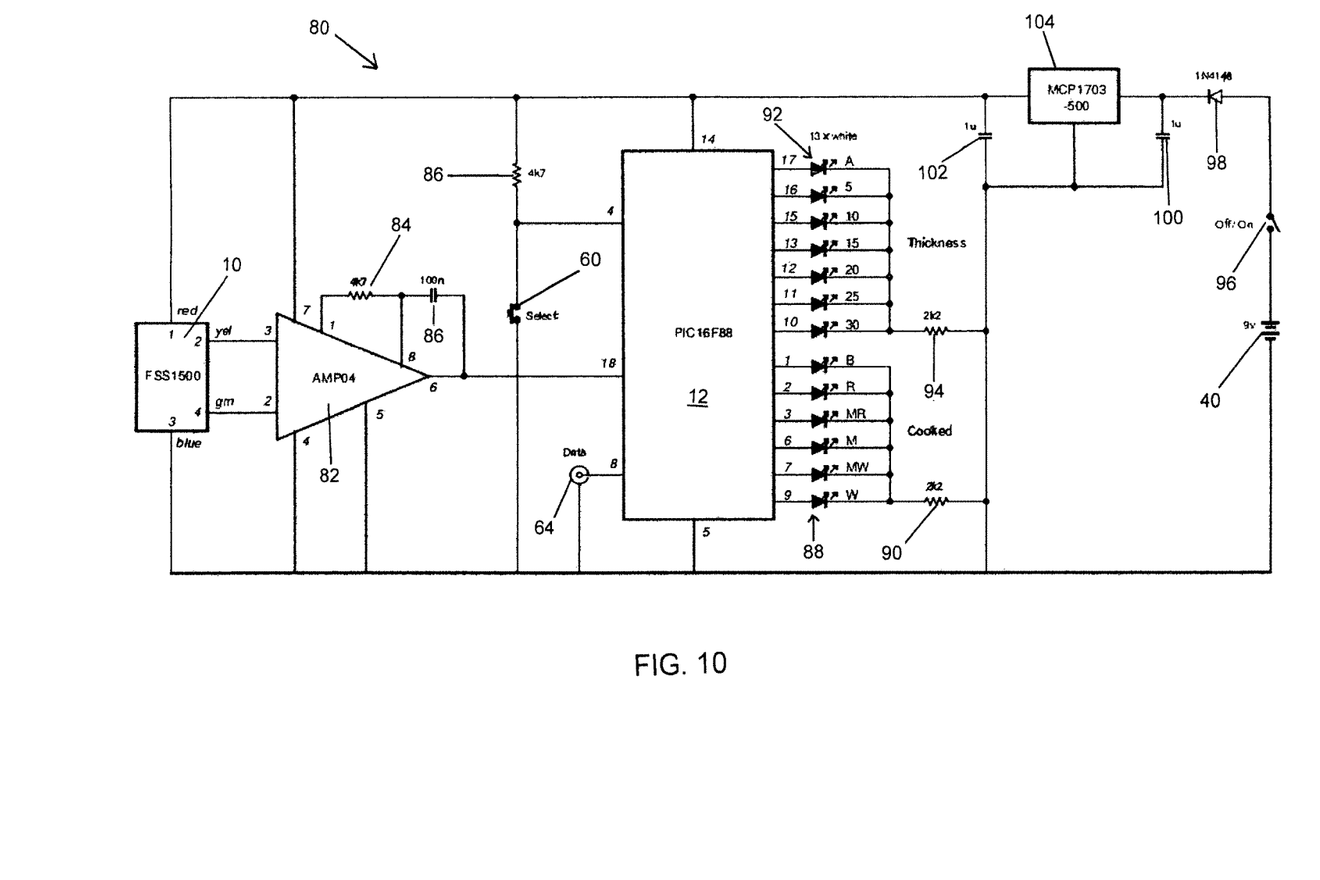
FIG. 10 is a circuit diagram of electrical circuit means able to be used in the apparatus of the present invention.

Referring now to FIG. 10, there is shown an electronic circuit 80 for use in the apparatus of the present invention. The circuit 80 shows the sensor means 10 and the microprocessor means 12. The sensor means 10 has outputs 1, 2, 3, 4 as marked. The sensor means 10 is shown connected to an amplifier 82. The amplifier 82 is connected to the microprocessor means 12 via a resistor 84 and a capacitor 86.

The electronic circuit 80 also shows the button 60 in circuit with a resistor 86.

The microprocessor means 12 has a lower portion with marked outputs 1, 2, 3, 6, 7, 9. These marked outputs extend through light emitting diodes 88 as shown to give the visual indications of blue, rare, medium rare, medium, medium well done and well done as shown. These indications are shown on the display means 14. These cooked indications are protected by a resistor 90.

The microprocessor means 12 is also shown provided with outputs 10, 11, 12, 13, 15, 16 and 17. These outputs go to light emitting diodes 92 which provide the outputs "A", 0.5, 1.0, 1.5, 2.0, 2.5 and 3.0. These outputs are thickness outputs. The thickness circuit is protected by a resistor 94 as shown. The apparatus 2 is calibrated differently for each thickness of the meat. A user selects a thickness, and the apparatus 2 then uses the correct calibration for that thickness.

The circuit 80 is shown with the battery 40. The battery 40 may be a 9 volt battery or any other suitable and appropriate battery. The circuit includes an on-off switch 96, a diode 98, capacitors 100, 102 and a linear voltage regulator. The linear voltage regulator 104 is a MCP1703-500. The linear voltage regulator 104 reduces the 9 volts from the battery 40 to 5 volts for the microprocessor means 12. The electronic circuit 80 shows further the jack 64 for inputting data and/or for charging the apparatus of the present invention.

In an embodiment of the invention, the apparatus is calibrated in ranges so that for instance 'medium' will be displayed when the sensor detects a level of resilience that is within the calibrated range of forces for that 'doneness' value. An example might be that the range of forces for 'medium' is designated as being between 400 g and 588 g (forces having been measured and calibrated in grammes). Thus if the sensor senses 412 g then the device would display the 'medium' value (led 'M' lights up). If the sensor were to detect a value of say 398 g then the next lower value would be displayed, i.e. Medium rare 'MR' because the range for MR is 312 g to 400 g. The upper and lower range values may be entered as a text data string using software via the data cable to a computer.

In an embodiment of the invention the apparatus may be made with two modes of operation, i.e. a normal mode and a program mode.

In the normal mode, the apparatus is how it will be used as a product. The user selects the thickness level and then takes a reading by pressing the probe against the meat surface. The device has a built-in time delay which allows the readings to 'settle' (as the meat surface "gives' in response to the probe pressing on it) that is, to reach a 'steady state'.

In the program mode, the apparatus enables a manufacturer to adjust the calibrations according to ongoing tests for accuracy and according to each thickness. The manufacturer is able to create a database of test data by testing cooked steaks and to use the average values to determine the upper and lower limits for the data ranges mentioned above. These data ranges are slightly different for each thickness. In the program mode, a manufacturer or a user are able to attach the device to a computer and enters data as strings of text. An example is shown below.

814_588_400_327_277_150_813_587_399_326_276_
149_812_587_398_325_275_148_811_586_397_324_
274_147_810_585_396_323_273_146_809_584_395_
322_272_145_808_583_394_321_271_144_3000_

The above is seven sets of six numbers plus the time delay. The seven sets of six numbers are the force ranges for each thickness, starting with 'well done' (any force above 814 g in this case will result in a well done display). The first range (814 g to 150 g) is for a thickness of 0.5 inches and the next is for 1 inch and so on to 3 inches. From the example above it can be seen that the upper and lower ranges for 'medium' (at 0.5 inches thickness) are the second and third numbers in the string (588 g and 400 g).

The last number in the string ('3000' in this case) is the time delay in milliseconds. 3000 ms is 3 seconds so the microprocessor means 12 captures the sensor's reading and displays the value according to the force detection after 3 seconds. In other words the meat surface and probe are allowed 3 seconds to 'settle', i.e. to reach a steady state level before the doneness level is displayed.

In an embodiment of the invention, the apparatus 2 may be provided with prevention means for preventing the probe 8 exerting too much force on the sensor means 10 and possibly damaging the sensor means 10. The prevention means may be an abutment device, for example a stopper, which prevents the probe 8 sliding too far into the apparatus 2, whereby the compression of the spring 16 is limited and the force by the probe 8 cannot exceed a safe limit. The abutment device in the form of a stopper may be positioned around the first portion 26 of the shank portion 24 of the probe 8. Alternatively an abutment formation could be produced by increasing the thickness of the lower part of the first portion 26. Alternatively a longer and lighter spring 15 could be employed to act as the prevention means, with the spring 16 then being able to absorb more inward movement of the probe 8 before any unduly high forces on the probe 8 were transferred to the sensor means 10. Alternatively, the desired protection of the sensor means 10 could be achieved using a shorter probe 8 so that the end 22 of the probe 8 becomes level with the flange 36 before a maximum safe force level is reached.

It is to be appreciated that the embodiments of the invention described above with reference to the accompanying drawings have been given by way of example only and that modifications may be effected. Thus, for example, the shape of the body 4, the meat-engaging formation 6, and the probe 8 may be varied. The visual display in the test result means 14 may be other than as shown in FIG. 9. The test result means 14 may alternatively or additionally be such as to give an audible result. The microprocessor means 12 may be another type of processor means. Other types of moisture-preventing means 72 may be employed such for example as one or more seals positioned on the probe 8 so that they are positioned between the probe 8 and the parts of the body 4 in which the probe 8 slides. The electrical components and values given in the electronic circuit 80 are given by way of example only, and other components and/or other values may be employed. The main portion 46 of the body 4 can be seen from FIG. 3 to be in two parts which are held together by screws 106. Other constructions for the main portion 46 of the body 4 may be employed. Individual components shown in the drawings are not limited to use in their drawings and they may be used in other drawings and in all aspects of the invention.

The invention claimed is:

1. Apparatus for testing the degree to which meat is cooked, which apparatus comprises:
   (i) a body;
   (ii) a meat-engaging formation which is fixed with respect to the body;
   (iii) a probe which is movable with respect to the body, and which is configured such that in use it does not penetrate the meat;
   (iv) sensor means for sensing the force applied by the meat to the probe when the meat-engaging formation is placed on the meat;
   (v) processor means which operates consequent upon the force sensed by the sensor means to provide an indication of the degree to which the meat is cooked;
   (vi) test result means for giving the indication provided by the processor means as a visual and/or audio test result; and
   (vii) selector means for selecting the approximate thickness of the meat.

2. Apparatus according to claim 1 in which the apparatus includes biasing means which biases the probe to a ready-for-use position in which the probe extends beyond the meat-engaging formation.

3. Apparatus according to claim 2 in which the probe is movable by sliding backwards and forwards in the body, and in which the biasing means is a spring biasing means.

4. Apparatus according claim 2 in which the biasing means acts on an end of the probe remote from the end of the probe that extends beyond the meat-engaging formation, and in which the end of the probe that extends beyond the meat-engaging formation is compressible to be level with an outer surface of the meat-engaging formation before the biasing means fully compresses, thereby to limit the force able to be exerted on the sensor.

5. Apparatus according to claim 4 in which the end of the probe that extends beyond the meat-engaging formation is a domed head, and in which the end of the probe remote from the domed head is the end of a shank portion of the probe.

6. Apparatus according to claim 2 in which the probe includes stop means for stopping the probe in the ready-for-use position.

7. Apparatus according to claim 1 in which the body is constructed for being held in a user's hand.

8. Apparatus according to claim 1 in which the meat-engaging formation is configured such that in use it does not penetrate the meat.

9. Apparatus according claim 1 in which the meat-engaging formation is a planar formation, a curved formation or a rounded formation.

10. Apparatus according claim 1 in which the sensor means is a piezo electric sensor means.

11. Apparatus according to claim 1 and which includes battery-receiving means for receiving at least one battery, whereby the apparatus is battery operated.

12. Apparatus according to claim 1 in which the display means is a visual display means.

13. Apparatus according to claim 1 and including time delay means whereby the microprocessor means captures the mean resistance reading from the sensor means after a predetermined time period which commences with when the meat-engaging formation is placed on the meat, whereby the meat surface is allowed to settle prior to a result being obtained.

14. Apparatus according to claim 1 and in which the selector means operates to control the processor means such that the values in the processor means for giving the indication of the degree to which the meat is cooked are re-set in dependence upon the selected meat thickness.

15. Apparatus according to claim 1 and including moisture-preventing means for preventing the entrance of moisture into the body via the probe, in which the moisture preventing-means is a cover which extends over the probe, and in which the cover is a resiliently-deformable cover.

* * * * *